United States Patent

Sivik et al.

[11] Patent Number: 5,965,767
[45] Date of Patent: Oct. 12, 1999

[54] BETA KETOESTER COMPOSITIONS AND METHOD OF MANUFACTURE

[75] Inventors: Mark Robert Sivik, Fairfield; Frederick Anthony Hartman, Cincinnati, both of Ohio

[73] Assignee: Procter & Gamble Company, Cincinnati, Ohio

[21] Appl. No.: 09/024,948

[22] Filed: Feb. 17, 1998

Related U.S. Application Data

[60] Provisional application No. 60/058,357, Sep. 10, 1997, and provisional application No. 60/043,874, Apr. 10, 1997.

[51] Int. Cl.$^6$ .................................................. C07C 69/74
[52] U.S. Cl. ............................................................. 560/126
[58] Field of Search ............................................ 560/126

[56] References Cited

U.S. PATENT DOCUMENTS

| | | | |
|---|---|---|---|
| 4,031,130 | 6/1977 | Renner et al. | 560/126 |
| 4,220,799 | 9/1980 | Berthold et al. | 560/126 |
| 5,118,833 | 6/1992 | Mori et al. | 560/51 |
| 5,144,057 | 9/1992 | Eyer | 560/51 |
| 5,183,929 | 2/1993 | Naito et al. | 560/178 |
| 5,194,671 | 3/1993 | Meier | 560/126 |
| 5,294,731 | 3/1994 | Paust et al. | 560/60 |
| 5,453,534 | 9/1995 | Eller | 560/187 |
| 5,492,690 | 2/1996 | Bush | 424/60 |

FOREIGN PATENT DOCUMENTS

| | | | |
|---|---|---|---|
| 324418 | 7/1989 | European Pat. Off. | C07C 69/72 |
| 376859 | 7/1990 | European Pat. Off. | C07C 69/72 |
| 514893 | 11/1992 | European Pat. Off. | C07C 67/343 |

OTHER PUBLICATIONS

"The Ester Enolate Carroll Rearrangement", by Wilson et al., J. Org Chem 1984, 49, pp. 722–725.

"The rearrangement of Allyl–Type Esters of β–Keto Acids", Kimel et al., J. Am. Chem. Soc., Oct. 1943, vol. 65, pp. 1992–1998.

*Primary Examiner*—Gary Geist
*Assistant Examiner*—Taylor V. Oh
*Attorney, Agent, or Firm*—Richard S. Echler, Sr.; Kim W. Zerby; Jacobus C. Rasser

[57] ABSTRACT

A method for making beta ketoesters of alcoholic actives, especially perfume alcohols, by a two step process involving a first diketene reaction step and a second carboxylic acid halide reaction step. The present invention also relates to mixtures of beta ketoesters of such alcoholic actives, especially those prepared by the present manufacturing process.

15 Claims, No Drawings

BETA KETOESTER COMPOSITIONS AND METHOD OF MANUFACTURE

This application claims the benefit of U.S. Provisional Application Nos. 60/058,357 filed Sep. 10, 1997 and 60/043,874 filed Apr. 10, 1997.

FIELD OF THE INVENTION

The present invention relates to a method for making beta-ketoesters of alcoholic actives, especially perfume alcohols. The present invention also relates to mixtures of beta-ketoesters of such alcoholic actives, especially those prepared by the present manufacturing process.

BACKGROUND OF THE INVENTION

Esters which release perfume alcohols are currently of interest for their different odor profiles in products, as well as their odor profiles during and after use. Particularly desirable are such esters which have a prolonged release characteristic from use in a home laundering process. Deposition on the fabric during the wash process followed by delayed release of the perfume after drying are included. The challenge for using such esters include not only the right combination of storage stability and odor release profile, but also the challenge of making such esters in a high yield, high purity, cost effective manner.

Beta ketoesters are a particularly desirable class of materials, but such materials can present a particular challenge for a cost effective production. The di-functionality (ketone and carboxylic ester functionality in the same compound) of these compounds limits the types of reactions and conditions under which these compounds can be made. Add on the industrial scale and cost constraints that the use of specialty reactants (like lithium salts) add to the possible synthesis methods, and the large scale of production of such beta ketoester compounds for use in high volume consumer products becomes problematic.

It has been discovered, however, that by the present invention there is a simple, high yield route to accomplishing the goal of affordable quantities of beta ketoester compounds of alcoholic actives, such as perfume alcohols. It is also possible by this method to prepare mixtures of beta ketoesters of perfume alcohols, allowing for further opportunities to create more complete odor profiles for consumer products (such as laundry and cleaning products) in a cost effective manner.

BACKGROUND ART

EP 514,893, published by Wacker Chemie GmbH on Nov. 25, 1992 relates to a process for the preparation of esters of β-ketocarboxylic acids starting from acetocarboxylic acid esters and carboxylic acid chlorides.

EP 324,418, published by Takeda Chemical Industries, Ltd on Jul. 19, 1989 describes a method of industrial production of tert-butyl 3-oxobutylate as an intermediate for synthesis of cephalosporin compounds. See also: "t-Butyl Acetoacetate", *Organic Synthesis* 1962, 42., Vol. V, pages 155–157, concerning acetoacetic acid, tert.-butyl esters.

"The Ester Enolate Carroll Rearrangement", by Wilson et al., *J Org Chem.* 1984, 49, pages 722–725, describes mild and high-yield synthesis of allylic acetoacetates and conditions for their rearrangement. See also: "The Rearrangement of Allyl-Type Esters of β-Keto Acids", Kimel et al., *J Am. Chem. Soc.*, Oct., 1943, Vol 65, pages 1992–1998.

EP 376,859, published by Eastman Kodak Company on Jul. 4, 1990, relates to nucleophiles which can be functionalized by contacting with specifically defined β-ketoester.

U.S. Pat. No. 5,492,690, to Bush, Feb. 20, 1996, describes pharmaceutical compositions comprising select beta ketoesters.

SUMMARY OF THE INVENTION

The present invention relates to a method for manufacturing beta ketoester compounds having the Formula (I):

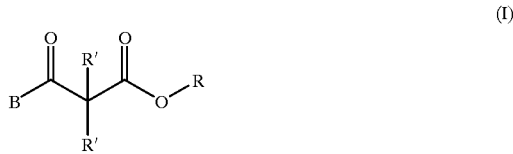

said method comprising the steps of:
(a) reacting one or more alcoholic actives, preferably a perfume alcohol, having the formula R—OH (wherein R has at least five carbon atoms, preferably R is selected from the group consisting of C5–30 linear, branched, substituted or unsubstituted alkyl, alkenyl, or aryl, and more preferably R—OH is a perfume alcohol), with a diketene having the formula:

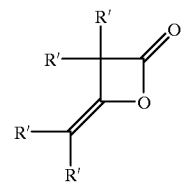

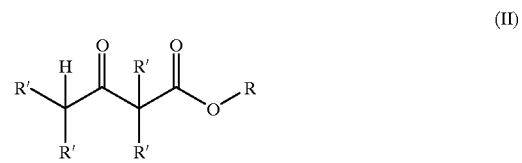

wherein each R' is independently selected from the group consisting of hydrogen and C1–30 linear, branched, substituted or unsubstituted alkyl, alkenyl, and aryl, and preferably all R' are hydrogen;
(b) reacting the beta ketoester having Formula (II) from step (a) with one or more carboxylic acid halides, preferably a carboxylic acid chloride, having the formula:

wherein B is selected from the group consisting of C1–30 alkyl, alkenyl, and aryl, linear or branched, substituted or unsubstituted, preferably B is selected from the group consisting of substituted or unsubstituted benzyl, phenyl, naphthyl, anisyl, octyl and nonanyl groups, more preferably B is selected from 1'-naphthyl, 2'-naphthyl, 4'-methoxyphenyl, 4'-nitrophenyl, and octyl, and X is selected from chloride or bromide, preferred X is chloride,
to produce a beta ketoester having the Formula (I).

The present invention also relates to mixtures of beta ketoester compounds having Formulas (I) and (II) as described hereinbefore, especially such mixtures prepared by the process according to the present invention.

All parts, percentages and ratios used herein are expressed as percent weight unless otherwise specified. All documents cited are, in relevant part, incorporated herein by reference.

DETAILED DESCRIPTION OF THE INVENTION

Step 1

Diketene Reaction

The first step of the present invention process involves the reaction of a diketene with an alcoholic active, preferably a perfume alcohol, to produce a beta ketoester having the Formula (II) as described hereinbefore. Preferred is the production of perfume alcohol esters of 3-oxobutyrate (i.e., wherein all the R' of Formula (II) are hydrogen).

By "alcoholic active", as used herein, is meant any compound having the formula R—OH, wherein R has at least 5 carbon atoms, and this alcohol has some desirable activity for example as a pharmaceutical active, insecticide, biocide, germicide, flavorant, or, preferably, a perfume agent. Preferred perfume alcohols include those wherein R is selected from C5–30 linear, branched, substituted or unsubstituted alkyl, alkenyl, or aryl. Preferably R is selected from C 10 linear, branched, substituted or unsubstituted alkyl, alkenyl, or aryl.

Specific perfume alcohols useful herein preferably include but are not limited by amyl alcohol; undecylenic alcohol; osyrol; sandalore; dihydro carveol; dihydro linalool; dihydromyrcenol; dihydro terpineol; dimetol; mycenol; alpha-terpineol; tetrahydro linalool; tetrahydro mugol; tetrahydro myrcenol; amyl cinnamic alcohol; decenol; trans-2-hexenol; patchomint; prenol; cuminyl alcohol; para-tolyl alcohol; phenylethyl carbinol; ethyl vanillin; isoamyl salicylate; para-hydroxyphenyl butanone; phenethyl salicylate; ethyl linalool; linalool; dihydromyrcenol; nerolidol; beta gamma hexenol; decyl alcohol; dihydro floralol; hawthanol; heptyl alcohol; isoamyl alcohol; isocyclo geraniol; isononyl geraniol; mayol; methyl lavendar ketone; octyl alcohol; phenyl propyl alcohol; rhodinol 70; rosalva; camelkol dh; cyclohexyl propyl alcohol; isobutyl benzyl alcohol; lavinol; phenyl ethyl methyl carbinol; propyl benzyl carbinol; iso pulegol; menthol; patchone; rootanol; roselea; trans decahydro beta naphthol; verdol; cinnamic alcohol; farnesol; geraniol; nerol; anisic alcohol; benzyl alcohol; undecavertol; eugenol; isoeugenol; and vanillin. More preferably, the perfume alcohol is selected from the group consisting of: beta gamma hexenol; decyl alcohol; dihydro floralol; hawthanol; heptyl alcohol; isoamyl alcohol; isocyclo geraniol; isononyl geraniol; mayol; methyl lavendar ketone; octyl alcohol; phenyl propyl alcohol; rhodinol 70; rosalva; camelkol dh; cyclohexyl propyl alcohol; isobutyl benzyl alcohol; lavinol; phenyl ethyl methyl carbinol; propyl benzyl carbinol; iso pulegol; menthol; patchone; rootanol; roselea; trans decahydro beta naphthol; verdol; cinnamic alcohol; farnesol; geraniol; nerol; anisic alcohol; benzyl alcohol; undecavertol; eugenol; isoeugenol; and vanillin. Most preferred alcohols include linalool, dihydromyrcenol, (α-terpineol, cis-3-hexenol, 9-decen-1-ol, geraniol, nerol and mixtures thereof Blends of alcoholic actives, as desired for the properties of the final product mixture manufactured by the present invention process, are encompassed by the present invention.

For example, the first step of the present invention process can include a method of producing a perfume ester of 3-oxobutyrate by allowing a perfume alcohol (e.g., linalool) to react with diketene in the presence of a 4-(tertiary amino)-pyridine. Specific examples of such pyridines include: 4-(dimethylamino)pyridine, 4-(diethylamino) pyridine, 4-(di-N-propylamino)pyridine, 4-(diisopropylamino)pyridine, 4-(N-methyl-N-ethylamino) pyridine, 4-(N-ethyl-N-n-propylamino)pyridine, 4-pyrrolidinopyridine, 4-(4-methylpyrrolidino)pyridine, and 4-piperidinopyridine. These 4-(tertiary amino)pyridines can be recovered after finishing this reaction and can be used repeatedly. Examples of preferred 4-(tertiary amino)pyridine include 4-(di-$C_{1-3}$alkylamino)pyridine such as 4-(dimethylamino)pyridine. 4-(Tertiary amino)-pyridine can accelerate the reaction in an catalytic amount, i.e., usually 0.001 to 1 mol. relative to 1 mol. of alcoholic active reactant, preferably 0.001 to 0.02 mol.

While such pyridine catalysts are preferred, other catalysts may be used. These include, for example, triethylamine, sodium acetate, tributylphosphine, sulfuric acid and titanium tetrachloride.

This reaction is preferably conducted in the absence of solvent, but it may be carried out in a non-protic organic solvent which does not give undesirable influence upon the reaction. Examples of such non-protic organic solvents include nitriles such as acetonitrile, ethers such as tetrahydrofuran, 1,2-dimethoxyethane, dioxane or diethylether, halogenated hydrocarbons such as methylene chloride, chloroform or carbon tetrachloride, esters such as ethyl acetate, butyl acetate, amides such as N,N-dimethylformamide or N,N-dimethylacetamide, hydrocarbons such as benzene, toluene, xylene, hexane or pentane, or a mixture of them. The volume of such non-protonic organic solvent to be used is in the range of from 0.2 to 20 relative to 1 mol. of alcoholic active reactant, preferably 1 to 5. The amount of diketene to be used is usually 1 mol. relative to 1 mol. of alcoholic active reactant, but it may be in the range of from 0.5 to 1.5 mol.

This reaction can also be carried out by adding diketene dropwise to a mixture of alcoholic active reactant and 4-(tertiary amino)pyridine, and, in this case the reaction can be attained even in the absence of solvent. The reaction temperature usually ranges from 0° to 100° C., preferably from 25° C. to 80° C. Since the reaction is an exothermic one, no heating is required at all for maintaining the above-mentioned temperature range. When the reaction temperature rises too high by the heat of the reaction, the reaction temperature can easily be adjusted within the range by using industrial cooling water or the like. For maintaining such reaction temperature, it is preferable to add diketene dropwise. The time required for this dropwise addition usually ranges from 0.2 to 10 hours, preferably 0.3 to 3 hours, while the range is not specifically limited so long as the object can be attained. By adjusting the rate of dropwise addition of diketene, the reaction can be allowed to proceed without heating or cooling. The reaction time after completing the dropwise addition of diketene varies with the solvent then used, reaction temperature, etc. but it usually ranges from 0.2 to 5 hours, preferably from 0.3 to 2 hours.

The thus-obtained ester of 3-oxo-carboxylic acid can be used as the material of the subsequent process step without further purification. Or, the reaction mixture can be used as the material of the subsequent process step after isolation and purification by means of, for example, concentration, distillation, pH-change, solvent-extraction, chromatography, etc.

Step 2

Reaction with Acid Halide

β-Keto esters of Formula (I) are obtained in very good yields if an acetocarboxylic acid ester is reacted with preferably calcium hydroxide or calcium oxide in an inert solvent, and the calcium complex that is formed is acylated with a carboxylic acid halide (preferably chloride) and then cleaved with an ammonium salt solution, with the formulation of the β-ketoesters having Formula (I).

Catalysts for this second step of the present invention process include, but are not limited to, sodium methoxide, sodium hydride, magnesium oxide, magnesium hydroxide, calcium oxide, calcium hydroxide and other divalent salts. Preferred reagents are calcium oxide and calcium hydroxide.

Preferred are processes wherein calcium hydroxide or calcium oxide is used in the presence of an organic solvent with the exclusion of water, and the calcium chelate complex of the beta ketoester of Formula (II) that is formed is acylated with a carboxylic acid chloride. The acylated calcium chelate complex is then cleaved, preferably with an aqueous ammonium salt solution.

The calcium compounds are suspended in an organic solvent under anhydrous conditions, whereby good distribution of the reactants is insured via mechanical movement. Aprotic solvents are preferably used. Examples of these are hydrocarbons such as hexane, heptane, isooctane; chlorohydrocarbons such as dichloromethane, 1,1,1-trichloroethane and trichloroethylene. Use can also be made of aromatic hydrocarbons, such as benzene or toluene, ethers such as diethyl ether, diisopropyl ether, methyl t-butyl ether, or tetrahydrofuran or ketones, such as isopropyl methyl ketone or isobutyl methyl ketone. Dichloromethane or mixtures of the designated solvents with dichloromethane are contemplated. Other preferred solvent mixtures are methyl t-butyl ether and methyl ethyl ketone; hexanes and methyl ethyl ketone.

The reaction takes place at temperatures of 0–50° C. or, preferably, at 20–30° C., whereby the reaction mixture is held at the reaction temperature by means of cooling. The calcium compound is preferably used in at least an equivalent quantity relative to the acetocarboxylic acid ester or, especially, in an excess quantity, especially in an excess quantity of up to 5 mol %.

The carboxylic acid halide (preferably the chloride having the formula B—(O)—Cl as described in detail hereinbefore) is preferably added to the suspension in at slightly less than an equivalent quantity based on the acetocarboxylic acid ester of Formula (II). Preferably the molar ratio of acid chloride to ester of Formula (II) is within the range of from about 0.5 to about 1.5, more preferably from about 0.60 to less than about 1, and most preferably from about 0.75 to about 0.99. The reaction temperature is 0–50° C., preferably 30–40° C. Blends of carboxylic acid halides are also within the present invention methods.

In order to form the desired β-ketocarboxylic acid esters of general formula (I), the suspension is then mixed with an aqueous solution of an ammonium salt, preferably ammonium formate, ammonium acetate or ammonium chloride, especially preferably with an aqueous ammonium chloride solution. The ammonium salt concentration in the solution preferably is 10–20 wt %. The ammonium salt is preferably used in an approximately equimolar quantity based on the acetocarboxylic acid ester. A pH value of 8.8–9.5 is set up in the suspension by means of an addition of a base, preferably ammonia or water-soluble primary or secondary amines, especially preferably aqueous ammonia. The reaction takes place with the formation of the β-ketocarboxylic acid ester at temperatures in the range from 0–50° C. or, preferably, 30–40° C. After terminating the reaction, the β-ketocarboxylic acid ester that is formed can be isolated, in pure form or as a mixture with the beta ketoester of Formula (II) according to the present invention, by means of conventional techniques such as extraction or concentration by evaporation. It can then be further purified, e.g., by means of fractional distillation/stripping.

In a further embodiment of the present invention, a desiccant, desiccating agent, or other means for removing water formed in the reaction sequence may be used to facilitate the formation of beta ketoesters of Formula (II). Non-limiting examples of desiccants include anhydrous inorganic salts such as calcium chloride, magnesium sulfate, etc. In addition, zeolites or "molecular sieves" having a pore size sufficient to absorb water, typically 3–4 angstroms, may also be used. Organic desiccants are also suitable for use in removing water formed in the present process. However, the use of a particular desiccant does not limit the formulator from using a desiccant in combination with other means for removing water formed in the reaction of Step 2 of the present invention. For example, a Dean-Stark trap for azeotropic removal of water may be suitably combined with one or more desiccant or desiccating agent. Also, more than one desiccant or desiccating agent may be combined or introduced at different stages during the course of the reaction depending upon the needs of the formulator.

Specific preferred β-ketoesters compounds of Formula (I) are nonlimitingly illustrated by the following: (±)-linalyl (2-naphthoyl)acetate; (±)-linalyl (1-naphthoyl)acetate; dihydromyrcenyl p-anisoyl)acetate; dihydromyrcenyl (4-nitrobenzoyl)acetate; dihydromyrcenyl (2-naphthoyl) acetate; (±)-linalyl (p-anisoyl)acetate; alpha-terpinyl (2-naphthoyl)acetate; beta-gamma-hexenyl (2-naphthoyl) acetate; 9-decen-1-yl (2-naphthoyl)acetate; and linalyl (nonanoyl)acetate.

EXAMPLE 1

Preparation of Linalyl (2-Naphthoyl)acetate

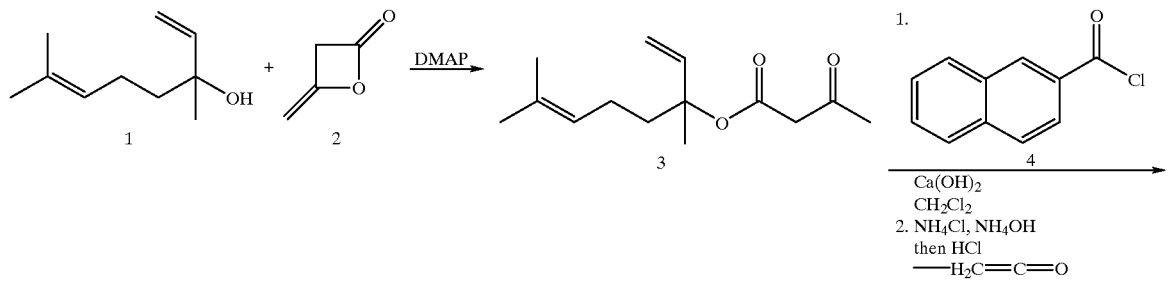

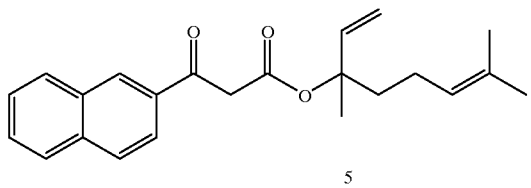

Linalyl acetoacetate (3). A mixture of linalool (100.00 g, 0.648 mol, Aldrich, 1) and 4-dimethylaminopyridine (0.40 g, 3.20 mmol, Aldrich, DMAP) in a 500 mL three-necked round-bottomed flask fitted with a condenser, argon inlet, addition funnel, magnetic stirrer and internal thermometer is heated to 55° C. Diketene (54.50 g, 0.648 mol, Aldrich, 2) is added dropwise in the course of 30 min. The mixture has a slight exotherm and turns from yellow to red during this time. After stirring an additional hour at 50° C., the mixture is cooled to room temperature. At this point, NMR analysis indicates the reaction is complete. The material from this lot is carried onto the next step. Purification of an earlier sample from this route by flash chromtography (elution with dichloromethane) yields linalyl acetoacetate of 92% yield and nearly colorless.

Linalyl (2-naphthoyl)acetate (5). Crude linalyl acetoacetate (154.51, 0.648 mol, 3) from above is placed in a 3000 mL three-necked round-bottomed flask fitted with a condenser, argon inlet, addition funnel, magnetic stirrer and internal thermometer. The contents are dissolved in 350 mL of dichloromethane and treated with powdered calcium hydroxide (50.44 g, 0.681 mol). The mixture is stirred at 30° C. for 30 min and then heated to 40° C. 2-Naphthoyl chloride (142.12 g, 0.746 mol, Aldrich, 4) dissolved in 20 mL of dichloromethane is added dropwise over 15 min. The mixture continues to be heated at this temperature for 1 h. Ammonium chloride (36.41 g, 0.681 mol) dissolved in 250 mL of water is added to the reaction mixture and the pH adjusted to ~9 with 28% ammonium hydroxide. After stirring 30 min at 35° C. the pH is adjusted to 1 with 20% HCl.

The mixture is transferred to a separatory funnel containing diethyl ether (500 mL) and water (500 mL). The layers are separated and the organic phase is washed with saturated NaHCO$_3$ solution (2×500 mL), dried over MgSO$_4$, filtered and concentrated by rotary evaporation to give a yellow red oil. At this point a light yellow solid precipitates from the mixture. An equal volume of hexane is added and the solids is collected by filtration and dried. NMR analysis indicates the solid is 2-naphthoic acid. The eluent is concentrated again by rotary evaporation to give a red oil. The oil is taken up in an equal volume of dichloromethane, passed through a plug of silica gel (400 g) and eluted with dichloromethane. The mixture is concentrated by rotary evaporation and stripped by Kugelrohr distillation (40° C., 0.10 mm Hg, 30 min) to yield 173.26 g (76.3%) of the product as a red oil; this product is a mixture of a 1:10 molar ratio of linalyl acetoacetate to linalyl (2-naphthoyl)acetate. A portion of this material is purified by column chromatography (elution with 2.5% ethyl acetate in hexanes) to give linalyl (2-naphthoyl) acetate as a light yellow oil.

EXAMPLE 2

Preparation of Dihydromyrcenyl (2-Naphthoyl) acetate

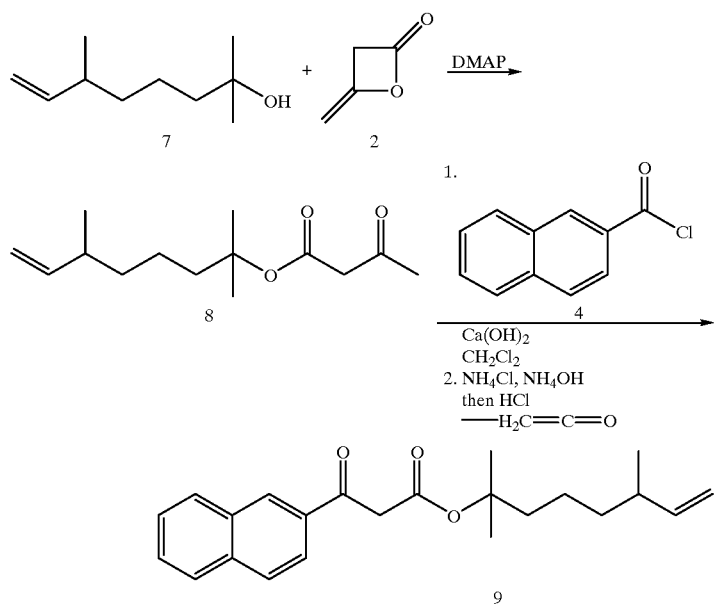

Dihydromyrcenyl acetoacetate (8). A mixture of dihydromyrcenol (37.88 g, 0.240 mol, Aldrich, 7) and 4-dimethylaminopyridine (0.16 g, 1.30 mmol, Aldrich, DMAP) in a 100 mL three-necked round-bottomed flask fitted with a condenser, argon inlet, addition funnel, magnetic stirrer and internal thermometer is heated to 50–60° C. Diketene (20.16 g, 0..240 mol, Aldrich, 2) is added dropwise in the course of 15 min. The mixture has a slight exotherm and turned from yellow to red during this time. After stirring an additional hour at 50° C., the mixture is cooled to room temperature. At this point, NMR analysis indicates the reaction is complete. Purification of the product mixture by flash chromatography (elution with dichloromethane) yields dihydromyrcenyl acetoacetate in 95% yield as a nearly colorless oil.

Dihydromyrcenyl (2-naphthoyl)acetate (9). Dihydromyrcenyl acetoacetate (27.00, 0.112 mol, 8) from above is placed in a 500 mL three-necked round-bottomed flask fitted with a condenser, argon inlet, addition funnel, magnetic stirrer and internal thermometer. The contents are dissolved in 60 mL of dichloromethane and treated with powdered calcium hydroxide (8.74 g, 0.118 mol). The mixture is stirred at 30° C. for 30 min and then heated to 40° C. 2-Naphthoyl chloride (25.13 g, 0.129 mol, Aldrich, 4) dissolved in 4 mL of dichloromethane is added dropwise over 15 min. The mixture continues to be heated at this temperature for 1 h. Ammonium chloride (6.31 g, 0.118 mol) dissolved in 45 mL of water is added to the reaction mixture and the pH adjusted to 9 with 28% ammonium hydroxide. After stirring 30 min at 35° C. the pH is adjusted to 1 with 20% HCl. The mixture is transferred to a separatory funnel containing diethyl ether (100 mL) and water (100 mL). The layers are separated and the organic phase is washed with saturated NaHCO$_3$ solution (2×100 mL), dried over MgSO$_4$, filtered and concentrated by rotary evaporation to give a yellow red oil. The oil is purified by column chromatography (elution with 5% ethyl acetate in hexanes) to give dihydromyrcenyl (2-naphthoyl)acetate as a light yellow oil.

What is claimed is:

1. A method for manufacturing β-ketoester compounds having the formula:

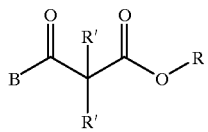

said method comprising the steps of:

(a) reacting one or more alcoholic actives having the formula R—OH, wherein R comprises from 5 to 30 carbon atoms, with a diketene having the formula:

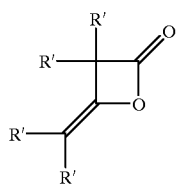

to produce a β-ketoester having formula:

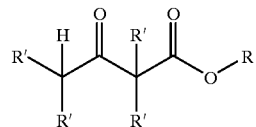

wherein each R' is independently selected from the group consisting of hydrogen and C$_1$–C$_{30}$ linear, branched, substituted or unsubstituted alkyl, alkenyl, and aryl; and (b) reacting said β-ketoester from step (a) with one or more carboxylic acid halides having the formula:

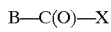

wherein B is selected from C$_1$–C$_{30}$ alkyl, alkenyl, and aryl, linear or branched, substituted or unsubstituted, and X is selected from chloride, bromide, and mixtures thereof, to produce a β-ketoester.

2. The method according to claim 1 wherein in step (b) the molar ratio of acid halide to ester having the formula:

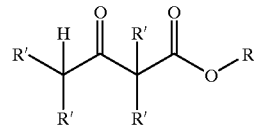

is from about 0.5:1 to about 1:1.5.

3. The method according to claim 2 wherein said molar ratio is from about 0.60:1 to less than about 1:1.

4. The method according to claim 3 wherein said molar ratio is from about 0.75:1 to about 0.99:1.

5. The product of the method according to claim 1 wherein the β-ketoester product is a mixture of esters having formula:

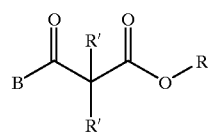

and the formula:

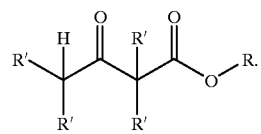

6. A method according to claim 1 wherein R is selected from the group consisting of C$_5$–C$_{30}$ linear, branched, substituted or unsubstituted alkyl, alkenyl, aryl, and mixtures thereof.

7. A method according to claim 1 wherein each R' is hydrogen.

8. A method according to claim 1 wherein said carboxylic acid halide is a carboxylic acid chloride.

9. A method according to claim 1 wherein B is selected from the group consisting of 1'-naphthyl, 2'-naphthyl, 4'-methoxyphenyl, 4'-nitrophenyl, octyl, and mixtures thereof.

10. A method for manufacturing β-ketoester compounds having the formula:

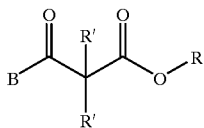

said method comprising the steps of:
(a) reacting an alcohol selected from the group consisting of linalool, tetrahydro-linalool, myrcenol, dihydromyrcenol, and mixtures thereof, with a diketene having the formula:

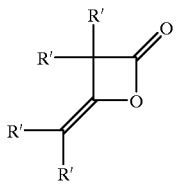

to produce a ,ketoester having formula:

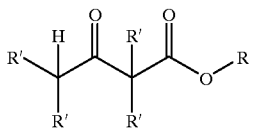

wherein the unit —OR is derived from said alcohol, each R' is independently selected from the group consisting of hydrogen and $C_1$–$C_{30}$ linear, branched, substituted or unsubstituted alkyl, alkenyl, and aryl; and
(b) reacting said β-ketoester from step (a) with one or more carboxylic acid halides having the formula:

wherein B is selected from 1'-naphthyl, 2'-naphthyl, 4'-methoxyphenyl, 4'-nitrophenyl, octyl, and mixtures thereof; and X is selected from chloride, bromide, and mixtures thereof, to produce β-ketoester.

11. A method according to claim 10 wherein B is 2'-naphthyl.

12. A method according to claim 10 wherein each R' is hydrogen.

13. A method according to claim 10 wherein said β-ketoester produced is 3,7-dimethyl-1,6-octadien-3-yl 3-(β-naphthyl)-3-oxo-propionate.

14. A method according to claim 10 wherein said β-ketoester produced is 2,6-dimethyl-7-octen-2-yl 3-(β-naphthyl)-3-oxo-propionate.

15. A method for manufacturing ,ketoester compounds having the formula:

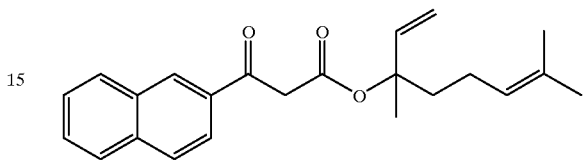

said method comprising the steps of:
a) reacting linalool with a diketene having the formula:

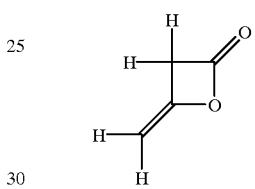

to produce a β-ketoester having formula:

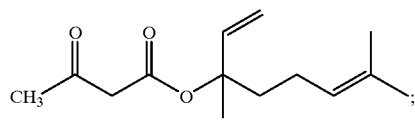

and
b) reacting said ,ketoester from step (a) with 2-naphthoyl chloride in the presence of calcium hydroxide to form 3,7-dimethyl-1,6-octadien-3-yl 3-(β-naphthyl)-3-oxo-propionate.

* * * * *